United States Patent
Yamaguchi

(10) Patent No.: US 9,023,283 B2
(45) Date of Patent: May 5, 2015

(54) RESONANT TYPE MASS SENSOR

(71) Applicant: Incorporated National University Iwate University, Morioka, Iwate-Prefecture (JP)

(72) Inventor: Masaki Yamaguchi, Morioka (JP)

(73) Assignee: Incorporated National University Iwate University, Morioka (JP)

( * ) Notice: Subject to any disclaimer, the term of this patent is extended or adjusted under 35 U.S.C. 154(b) by 0 days.

(21) Appl. No.: 14/081,573

(22) Filed: Nov. 15, 2013

(65) Prior Publication Data
US 2014/0234171 A1  Aug. 21, 2014

(30) Foreign Application Priority Data
Feb. 16, 2013  (JP) ................... 2013-028481

(51) Int. Cl.
G01N 15/06  (2006.01)
G01N 33/00  (2006.01)
G01N 33/48  (2006.01)
G01N 19/00  (2006.01)

(52) U.S. Cl.
CPC ..................................... *G01N 19/00* (2013.01)

(58) Field of Classification Search
CPC ........ G01N 15/06; G01N 33/00; G01N 33/48
USPC ......... 422/50, 68.1, 82.01, 83, 98; 436/43, 63
See application file for complete search history.

(56) References Cited

FOREIGN PATENT DOCUMENTS

| JP | 3298897 B2 | 7/2002 |
|---|---|---|
| JP | 2005-533265 A | 11/2005 |
| JP | 4638281 B2 | 2/2011 |

OTHER PUBLICATIONS

"Quarts Crystal Microbalance", Nov. 12, 2013, http://www.tamadevice.co.jp/9mhz.htm.

*Primary Examiner* — Brian J Sines
(74) *Attorney, Agent, or Firm* — Westerman, Hattori, Daniels & Adrian, LLP

(57) ABSTRACT

A separate excitation and high sensitive resonant type mass sensor is provided. The resonant type mass sensor 1 includes: an oscillator 3; a vibrator 2 placed on the oscillator 3; and a detecting unit 5 for detecting the resonant frequency of the vibrator 2, and is characterized in that the vibrator 2 and the oscillator 3 are not coupled mechanically and that the vibrator 2 is not mechanically coupled to any members. The vibration of the vibrator 2 is represented by a standing wave. The vibrator 2 includes a molecular recognition means for recognizing the molecules of a substance to be measured. The molecular recognition means may collect specific molecules by antigen-antibody reaction. The vibrator 2 may include at least a magnetizable part. To the magnetizable part, magnetic beads 26, to which an antibody or antigen is immobilized, may be adsorbed magnetically. The detecting unit 5 is made up of a light-emitting device and a photo-sensitive device, and may include a means to detect any one of frequency, displacement, velocity, and acceleration.

19 Claims, 20 Drawing Sheets

(a)

Number of nodes: 2
Primary mode (b)

Number of nodes: 3
Secondary mode (c)

Number of nodes: 4
Third-order mode (a)

(b)

RESONANT TYPE MASS SENSOR

This application claims the benefit of Japanese Application No. JP 2013-28481 filed, in Japan on Feb. 16, 2013, of which is hereby incorporated by reference in this entirely.

TECHNICAL FIELD

The present invention relates to a resonant type mass sensor.

PRIOR ART

A resonant type mass sensor has been used for a method of measuring the concentration of a trace amount of chemical substances contained in gas or liquid. This sensor utilizes the fact that when another material attaches to a vibrator that is vibrating at a certain frequency, the resonant frequency also changes in accordance with the slight change in mass. As vibrators, a self excitation type vibrators such as a quartz crystal microbalance (QCM) and those generated by connecting an oscillator, such as a piezoelectric element, to the vibrator. The vibrator such as a cantilever made of ceramics has been used. The former can be called the self excitation type mass sensor, whereas the latter can be called a separate excitation type mass sensor.

The self excitation type mass sensor equipped with a thin-film resonator made of a piezoelectric material as the vibrator is disclosed in JP 2005-533265 A, for example. Furthermore, the mass sensor wherein the vibration is caused by a driving section electrostatically coupling to a Si oscillator is disclosed in JPB 4638281. The separate excitation type mass sensor coupling to the oscillator made of the piezoelectric element connected to the vibrator is disclosed in JPB 3298897, for example.

The absolute value of resonant frequency of the vibrator decreases in proportion to the decreasing of the mass of the target material. Consequently, a method of fastening the vibrator, a power feeding method, and environmental factors such as temperature and humidity affect the sensitivity limit of measurement, which is common to all these resonant type mass sensors.

However, with mass sensors based on the prior art, the power is fed to the vibrator itself (See the self excitation type mass sensor, Tama Device Co., Ltd. Japan, http://tamadevice-.co.jp/9mhz.htm), or to the piezoelectric element mechanically fastened (by adhesion) to the vibrator (the separate excitation type mass sensor). Owing to these reasons, the maintaining these electrical supply lines inhibits resonant phenomena, thereby disturbing improvement in sensitivity.

In addition, the separate excitation type mass sensors include those that excite the vibrator magnetically and not electrically (See J. Teva, et al, "A femtogram resolution mass sensor platform, based on SOI electrostatically driven resonant cantilever," Ultramicroscopy, Vol. 106, pp. 800-807, 2006). However, in this type, it is necessary that the gap between the vibrator and a magnetic head must be positioned very accurately.

As described above, in the conventional separate excitation type mass sensor, it is necessary to fasten the vibrator to a housing, which inhibits resonant phenomena, thus disturbing improvement in sensitivity.

SUMMARY OF INVENTION

In consideration of the above mentioned problem, the object of the present invention is to provide a separate excitation type resonant type mass sensor having a high-sensitivity.

The present inventor has thought upon the present invention by discovering that by exciting the resonant frequency of a microbeam, namely an vibrator whose both ends are free, in the transverse vibration mode excited by a piezoelectric element, the resonant type mass sensor having 38.8 ng/Hz measurement sensitivity can be achieved.

In order to realize the above-mentioned objectives, the present invention provides a resonant type mass sensor comprising: an oscillator; an vibrator placed on the oscillator; and a detecting unit for detecting the resonant frequency of the vibrator, and characterized in that the vibrator and the oscillator are not coupled mechanically, and the vibrator is not coupled mechanically to any of other members.

In the above mentioned aspect, the vibration of the vibrator is preferably represented by a standing wave.

The vibrator is preferably equipped with a molecular recognition means for recognizing the molecules of a substance to be measured.

The molecular recognition means preferably uses an antigen-antibody complex reaction.

The vibrator preferably includes at least a magnetizable part. To the magnetizable part, magnetic beads, to which an antibody or antigen is immobilized, are preferably adsorbed magnetically.

The detecting unit preferably includes a light-emitting device and a photo-sensitive device, and is equipped with a means to detect any one of oscillation, displacement, velocity, and acceleration.

According to the resonant type mass sensor of the present invention, since there is no need to fasten the vibrator to the oscillator, resonant phenomena are not prohibited by power supply or fastening, limitation in design of shape and dimensions of the vibrator can be eliminated, and the change in mass can be measured highly sensitively. Furthermore, since the vibrator is not fastened to the oscillator, the vibrator can be replaced quite easily.

MODES FOR CARRYING OUT THE INVENTION

The embodiments of the present invention will hereafter be described in detail by referring to drawings.

The First Embodiment

Figure 1:
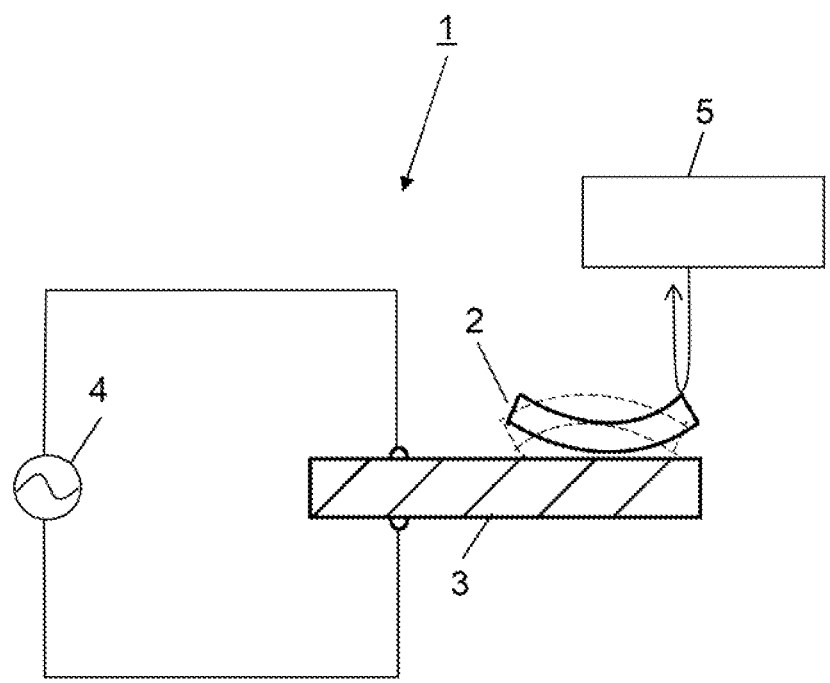
FIG. 1 is a block diagram showing the structure of a resonant type mass sensor according to the first embodiment of the present invention.

FIG. 1 is a block diagram showing the structure of a resonant type mass sensor 1 according to the first embodiment of the present invention. As shown in FIG. 1, the resonant type mass sensor 1 of the present invention includes: a vibrator 2; an oscillator 3 for exciting the vibrator 2; a power supply 4 for driving the oscillator 3 for excitation; and a detecting unit 5 for detecting the vibration of the vibrator 2. The vibrator 2 of the resonant type mass sensor 1 of the present invention is placed on the oscillator 3. The vibrator 2 and the oscillator 3 are not coupled mechanically, and the vibrator 2 is not coupled to any members mechanically, namely, the vibrator 2 is not fastened to any part in the structure. The vibrator 2 is made into a shape and dimensions optimum for resonant phenomena as described later. The vibrator 2 is disposed on the oscillator 3 such as a piezoelectric element in unrestricted state. When the piezoelectric element vibrates at a given frequency, it is constructed that the vibrator 2 can vibrate at the resonant frequency of the vibrator 2 itself. When alternating voltage having frequency close to the frequency of vibration in the normal mode of the vibrator 2, which has a shape of a microbeam, is applied to the piezoelectric element 3, the vibrator 2 resonates at the resonant frequency unique to itself. In other words, the vibrator 2 is excited by the oscillator 3 around the resonant frequency of the vibrator 2. Furthermore, it is not necessary that the oscillator 3 vibrates at a frequency close to the resonant frequency of the vibrator 2. In this way, the vibrator 2 is made to be free from any restrictions on materials, shape, and dimensions, which improve the degree of freedom in design significantly.

Meanwhile, the vibration mode of the vibrator 2 is set not to be in a single-axis vibration mode where the transfer is made in a certain direction as in the case of a standing wave type ultrasonic motor. Namely, since the vibration mode of the vibrator 2 is not the vibration mode where transfer is made in a certain direction and the amplitude is as small as on nanometer (nm) order, the vibrator 2 never comes off the oscillator 3.

When the vibrator 2 is exposed to a measurement sample in a liquid or gas form, or when the measurement sample attaches to the vibrator 2, the mass of the vibrator 2 increases. Consequently, the resonant frequency of the vibrator 2 changes, and then the concentration of a specific chemical substance in the sample can be estimated by the change rate of the resonant frequency. The change in the resonant frequency of the vibrator 2 is detected by the detecting unit 5. As a means to measure the resonant frequency of the vibrator 2, the detecting unit 5 can use an optical detecting means made up of a light-emitting device and a photo-sensitive device. The optical detecting means may measure any one of the frequency, displacement, velocity, and acceleration of the vibrator 2. As the detecting means 5, a laser displacement gauge, etc. may be used. By using a laser displacement gauge, non-contact measurement of the change in the resonant frequency of the vibrator 2 can be made.

(Vibration Mode of the Vibrator)

The vibration mode of the vibrator 2 of the present invention will be described.

Figure 2:
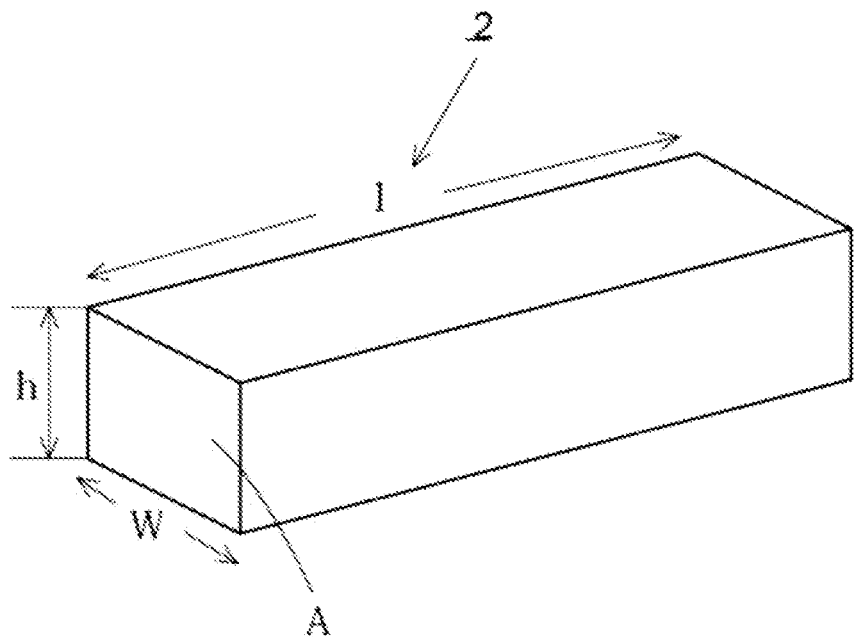
FIG. 2 is a diagrammatic perspective view describing the shape of the vibrator of the present invention.

FIG. 2 is a diagrammatic perspective view describing the shape of the vibrator 2 of the present invention. As shown in FIG. 2, the vibrator 2 of the present invention has a shape of an elongated pillar i.e. a microbeam having length l, which is the longer direction, width w, height h, and cross-sectional area A, for example. As the vibrator 2 of the present invention, piezoelectric crystals, etc. can be used. Piezoelectric crystals include crystal and PZT. The vibration mode of the vibrator 2 of the present invention is a transverse vibration mode which vibrates in a direction perpendicular to the longitudinal direction of the microbeam, and its resonant frequency (fn) is given by the formula (1) as shown below. The transverse vibration mode is also called as the bending vibration.

$$f_n = \frac{\lambda_n^2}{2\pi d^2} \sqrt{\frac{EI}{\rho A}} \quad [\text{Hz}] \tag{1}$$

The symbols in the formula (1) as shown above represent the following.

n: Mode order of vibration system (See FIG. 3.)

$\lambda_n$: $\lambda_1$=4.730, $\lambda_2$=7.583, and $\lambda_3$=10.996 under the condition where both ends are free l: Length of the vibrator 2 (cm)

E: Longitudinal elastic modulus (crystal: 9.72×10$^{11}$) (g/cm·s$^2$)

I: Second moment of area (cm$^4$)

ρ: Density (crystal: 2.65) (g/cm$^3$)

A: Cross-sectional area of microbeam (cm$^2$)

In addition to the transverse vibration mode used for the vibrator 2 of the present invention, the longitudinal vibration mode, which is the stretching vibration of the microbeam, and the torsional vibration mode caused by torsion of the microbeam are generated. The frequency in the transverse vibration mode used for the vibrator 2 of the present invention is set so as to be different from those in the longitudinal vibration mode and in the torsional vibration mode of the vibrator 2.

The resonant frequency (fn) of the longitudinal vibration, namely stretching vibration of the microbeam, is represented by the formula (2) as shown below.

$$f_n = \frac{\lambda_n}{2\pi d}\sqrt{\frac{E}{\rho}} \quad [\text{Hz}] \tag{2}$$

In the above formula, $\lambda_n$ is as follows under the condition where both ends are free: $\lambda_1=\pi$, $\lambda_2=2\pi$, and $\lambda_3=3\pi$.

The resonant frequency (fn) of the torsional vibration of the microbeam is represented by the formula (3) as shown below.

$$f_n = \frac{\lambda_n}{2\pi d}\sqrt{\frac{G}{\rho}} \quad [\text{Hz}] \tag{3}$$

In the above formula, $\lambda_1=\pi$, $\lambda_2=2\pi$, and $\lambda_3=3\pi$ under the condition where both ends are free, and G represents modulus of transverse elasticity (g/cm·s$^2$). Here, G of crystal is $2.95 \times 10^{11}$ (g/cm·s$^2$).

(Mode Order of transverse Vibration of the Vibrator)

The mode order when the vibrator 2 of the present invention is in the transverse vibration mode will be described.

Figure 3:
FIG. 3 is a chart describing the mode order of the vibrator of the present invention having free ends in the transverse vibration mode, wherein (a) explains the primary mode, (b) the secondary mode, and (c) the third-order mode.
Figure 3:
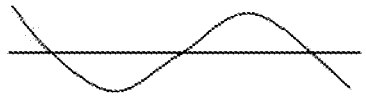
Figure 3:

FIG. 3 is a chart describing the mode order of the vibrator 2 of the present invention having free ends in the transverse vibration mode when both ends are free, wherein (a) explains the primary mode, (b) the secondary mode, and (c) the third-order mode.

As shown in FIG. 3, the transverse vibration of the vibrator 2 of the present invention is represented by a standing wave when both ends are free, and the number of nodes of the primary mode is 2, that of the secondary mode is 3, and that of the third-order mode is 4.

(Resonant Frequency of the Vibrator in the Transverse Vibration Mode)

The crystal was selected as the material of the vibrator 2, and the resonant frequencies in the primary mode to the third-order mode of the transverse vibration mode were calculated using the formula (1) as shown above when the length of the microbeam was 4 mm, its width was 0.4 mm, and its height was 0.4 mm. Table 1 summarizes the calculation results of transverse vibration mode with the values of the longitudinal vibration mode and the torsional vibration mode.

TABLE 1

| Dimensions l × h × w (mm) | n | Transverse vibration f(kHz) | Longitudinal vibration f(kHz) | Torsional vibration f(kHz) |
|---|---|---|---|---|
| 4 × 0.4 × 0.4 | Primary | 156 | 757 | 417 |
| | Secondary | 400 | 1514 | 834 |
| | Third-order | 841 | 2271 | 1251 |

As shown in Table 1, the resonant frequency of the vibrator 2 in the transverse vibration mode increases with the increase of the mode order, and its value is different from the values in the longitudinal vibration mode and the torsional vibration mode.

According to the resonant type mass sensor 1 of the present invention, by be unnecessary mechanical fixing the vibrator 2 to the oscillator 3, the inhibition on resonant phenomena due to supply of power or fastening can be eliminated along with the restrictions on the design of shape and dimensions of the vibrator 2. Consequently, change of the mass can be measured with high sensitivity. Furthermore, since the vibrator 2 is not fastened to the oscillator 3 mechanically, the vibrator 2 can be replaced quite easily.

The Second Embodiment

Figure 4:
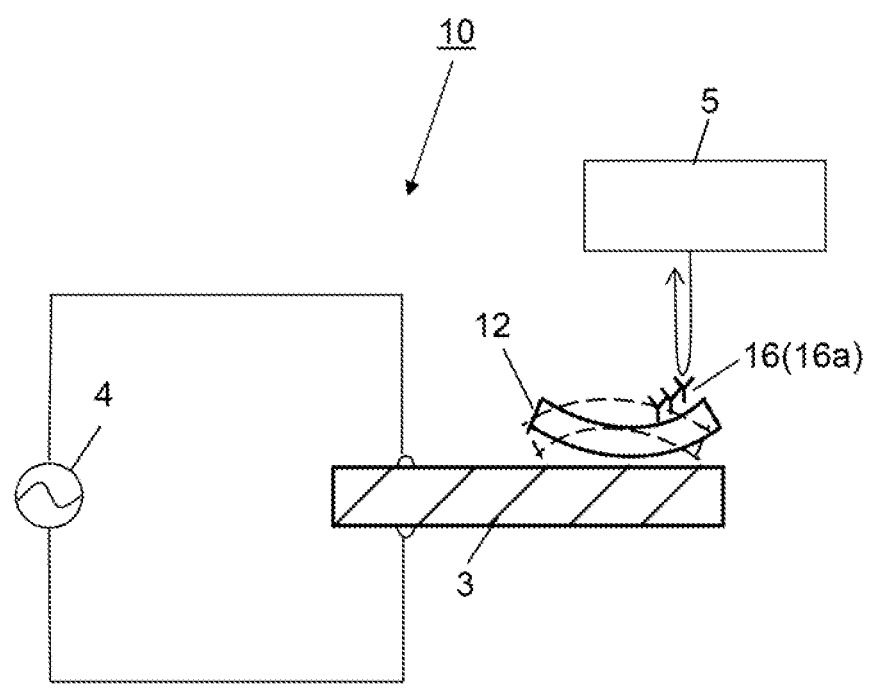
FIG. 4 is a block diagram showing the structure of a resonant type mass sensor according to the second embodiment of the present invention.

FIG. 4 is a block diagram showing the structure of a resonant type mass sensor 10 according to the second embodiment of the present invention. As shown in FIG. 4, the resonant type mass sensor 10 in the second embodiment differs from the resonant type mass sensor 1 as shown in FIG. 1 in that a molecular recognition device 16 such as an antibody is fastened to the surface of the vibrator, forming an antibody-immobilized vibrator 12. In other words, the molecular recognition means 16 for recognizing the molecules of the substance to be measured is provided in the second embodiment. The molecular recognition means 16 includes an antibody 16a and an antigen for example, and collects specific molecules by antigen-antibody complex reaction. In the case as shown by the figure, the molecular recognition device 16 such as antibody 16a is immobilized to the surface of the vibrator 12 such as free ends i.e. at a position where the amplitude is large. The antibody and/or antigen constituting the molecular recognition means 16 may be immobilized to the surface of the vibrator 12.

(Method of Immobilizing the Antibody)

A method of immobilizing the antibody 16a to the vibrator 12 will be described. The antibody 16a can be immobilized to the vibrator 12 by the method comprising:

forming a thin metallic film on the surface of the vibrator 12;

forming a molecular film on the order of monomolecular layer on this metal film by sputtering, etc.; and modifying the antibody 16a to this molecular layer.

An adhesion layer and a platinum (Pt) film formed on the adhesion layer can be used as the metallic thin film. Ti, Cr, etc. may be used as the adhesion layer. As the molecular film on the order of monomolecular layer, a self-assembled monolayer (hereinafter called as the SAM layer) can be used.

(Specific Example of the Method of Immobilizing the Antibody)

An example of the method of immobilizing the antibody 16a will be described.

Titanium (Ti) and platinum (Pt, 500 Å) are deposited by the sputtering method to form a film on one of the surfaces of the microbeam-like vibrator 12. To immobilize the antibody 16a on the surface of the platinum, the SAM film is formed and the antibody 16a is modified on the SAM film. The amine coupling process was used to couple the SAM film and the antibody 16a. In addition, to prevent unnecessary protein from attaching, thus adversely affecting the measurement, the blocking was performed by using an ethanolamine solution, and the blocking using a bovine serum albumin (BSA) solution was also performed.

The typical process of forming the SAM film on the microbeam-like vibrator 12 and modifying the antibody 16a will hereafter be described further in detail.

(1) Removing organic materials: The surface of the electrode is immersed in a piranha solution for 15 minutes to remove organic materials.

(2) Storage method: Immediately after the electrode is washed using distilled water, it is dried using nitrogen gas, and immersed in distilled water for storage until a SAM film is formed. The storage time is one hour or shorter.

(3) Formation of a SAM film: 1 mmol/L ($10^{-3}$ mol/L) of 5-carboxy-1-decanethiol dissolved in ethanol is dropped, and the electrode is immersed in the solution in a constant-temperature bath of 25° C. for one hour.

(4) Removing unreacted materials: The surface of the electrode is washed using ethanol to remove unreacted materials.

(5) Activation: After the electrode is washed using distilled water, a mixed solution (1:1) of an N-hydroxysuccinimide (NHS) aqueous solution and a 1-ethyl-3-(3-dimethylaminopropyl) carbodiimide (WSC) aqueous solution is dropped, and the electrode is immersed in the solution in the 25° C. constant-temperature bath for one hour.

(6) Immobilizing antibody 16a: After the item is washed using phosphate buffered saline (PBS), antibody 16a diluted by PBS is dropped, and the electrode is immersed in the solution in the 25° C. constant-temperature bath for 30 minutes.

(7) Inactivation: After the electrode is washed using the PBS, the item is immersed in a 20% ethanolamine aqueous solution in the 25° C. constant-temperature bath for one hour to inactivate residual active ester.

(8) Blocking process: After the electrode is washed using distilled water, a 1% BSA aqueous solution is dropped, and the electrode is immersed in the solution at 4° C. for 90 minutes.

Figure 5:
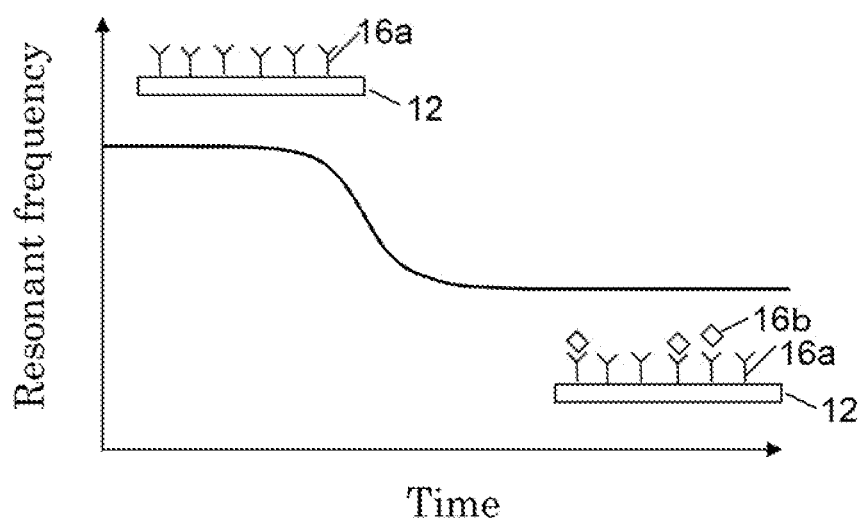
FIG. 5 is a chart showing the time change in the resonant frequency of the vibrator of the resonant type mass sensor according to the second embodiment of the present invention.
Figure 6:
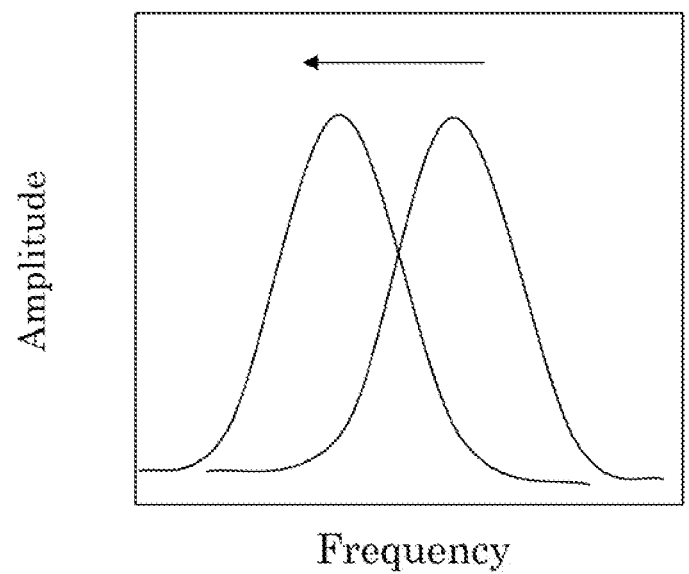
FIG. 6 is a chart showing the change in resonant frequency of the vibrator at the time of antigen-antibody complex reaction.

FIG. 5 is a chart showing the time change of the resonant frequency of the vibrator 12 of the resonant type mass sensor 10 according to the second embodiment of the present invention. FIG. 6 is a chart showing the change in the resonant frequency of the vibrator 12 during the antigen-antibody complex reaction.

As shown in FIG. 5, in the resonant type mass sensor 10, when the vibrator 12 is exposed to a gas or liquid measurement sample, then specific molecules contained in the measurement sample, the antigen 16b, for example, are trapped by immune reaction (also called as immunoassay) such as the antigen-antibody complex reaction. The mass of the vibrator 12 increases. As a result, as shown in FIG. 6, the resonant frequency of the vibrator 12 decreases. The concentration of specific chemical substances in the measurement sample can be estimated by the rate of change of the resonant frequency. The change of the resonant frequency of the vibrator 12 is detected by the detecting unit 5 as in the case of the resonant type mass sensor 1 as shown in FIG. 1. When a laser displacement gauge is used as the detecting unit 5, for example, the non-contact measurement of the change of the resonant frequency of the vibrator 12 can be performed.

In the above description, the SAM film was formed on the microbeam-like vibrator 12 and then the antibody 16a was modified on the SAM film. However, the antigen 16b may be modified on the microbeam-like vibrator 12.

According to the resonant type mass sensor 10 of the present invention, after the mass of specific molecules contained in the above measurement sample is measured, the vibrator 12, to which the antibody 16a is immobilized, can be reused. For example, the antigen 16b, namely molecules to be measured, can be removed in several minutes by immersing the used antibody-immobilized vibrator 12 in a dissociation solution of antigenic agent of a given concentration. Then, the separate excitation resonant type mass sensor 10 can be reused. The concentration of the dissociation solution of antigenic agent can be determined depending on the type of the antigen 16b to be measured.

The Third Embodiment

Figure 7:
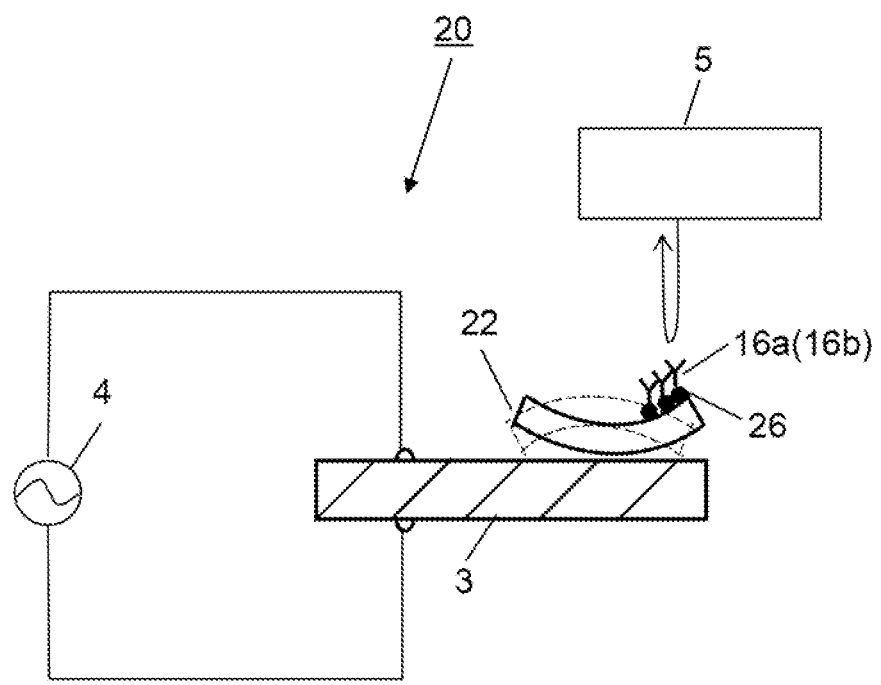
FIG. 7 is a block diagram showing the structure of a resonant type mass sensor according to the third embodiment of the present invention.

FIG. 7 is a block diagram showing the structure of a resonant type mass sensor 20 according to the third embodiment of the present invention. The resonant type mass sensor 20 as shown in FIG. 7 differs from the resonant type mass sensor 1 as shown in FIG. 1 in that the vibrator 22 has a magnetic property. A magnetic measurement sample can be adsorbed onto the vibrator 22 by the magnetic force, and the mass of the magnetic measurement sample can be measured. The magnetic measurement sample solution can be used as such a magnetic measurement sample. The magnetic measurement sample solution is obtained by mixing a sample solution containing an antigen 16b, and the magnetic bead solution containing an antibody 16a and magnetic particles such as magnetic beads 26 (See FIG. 11.).

The vibrator 22 can be constructed by including at least a magnetizable part. Magnetic beads 26, to which the antibody 16a or antigen 16b is adsorbed, may be adsorbed magnetically to this magnetizable part. The vibrator 22 made of a ferromagnetic material may be used as the vibrator. The ferromagnetic materials that can be used for the vibrator 22 include soft iron, silicon steel, ferrite, cobalt, nickel, and alnico magnet.

(Method of Fabricating the Ferromagnetic Vibrator)

Figure 8:
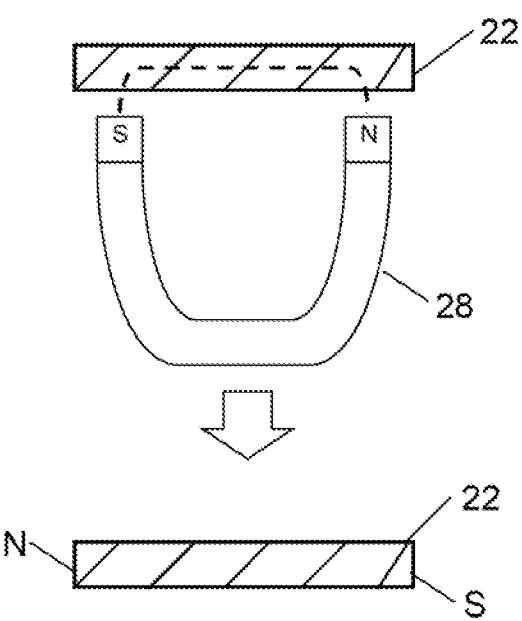
FIG. 8 is a chart showing a method of fabricating the ferromagnetic vibrator.

FIG. 8 is an illustration showing a method of fabricating the ferromagnetic vibrator 22. As shown in FIG. 8, the ferromagnetic vibrator 22 is fabricated by forming a vibrator made of a ferromagnetic material into a shape allowing a given resonant frequency to be obtained, and then the fabricated ferromagnetic vibrator 22 is magnetized using a permanent magnet 28 or an electromagnet.

Figure 9:
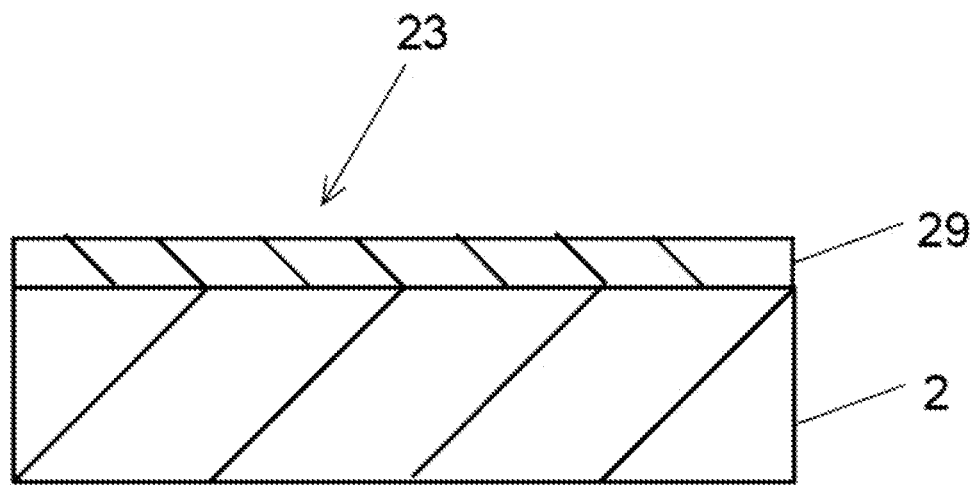
FIG. 9 is a cross-sectional view showing a variation of the vibrator of the resonant type mass sensor.

FIG. 9 is a cross-sectional view of a variation of the vibrator of the resonant type mass sensor 20 as shown in FIG. 7. As shown in FIG. 9, this ferromagnetic vibrator 23 has a structure where a non-magnetic vibrator 2 is covered with a magnetic thin film 29. As the non-magnetic vibrator 2, the piezoelectric crystal, etc. may be used as in the case of the vibrator 2 as shown in FIG. 1. Such piezoelectric crystals include quartz and PZT etc.

(Another Method of Fabricating the Ferromagnetic Vibrator)

Figure 10:
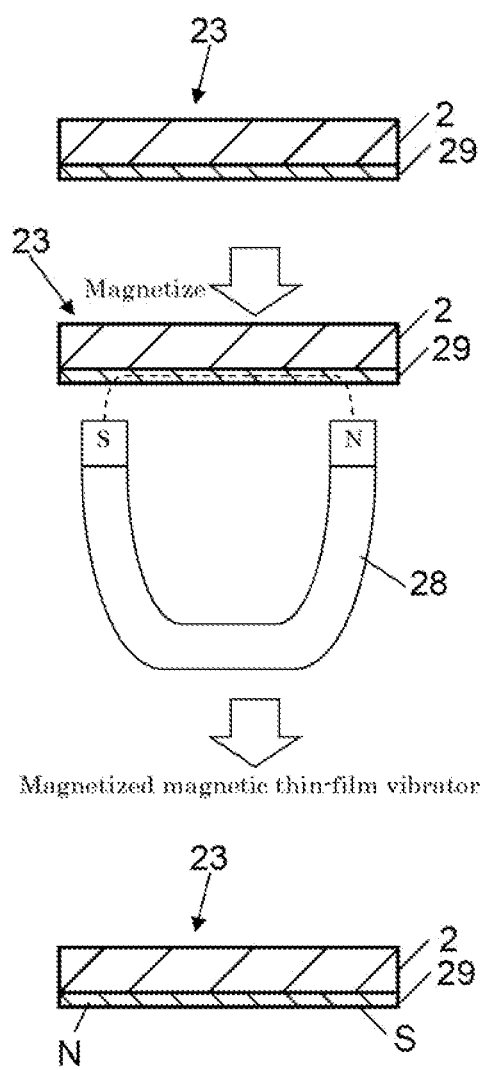
FIG. 10 is a chart showing a method of fabricating the ferromagnetic vibrator shown in FIG. 9.

FIG. 10 is an illustration showing a method of fabricating the ferromagnetic vibrator 23 as shown in FIG. 9. As shown in FIG. 10, the ferromagnetic vibrator 23 is fabricated by following process as shown below.

(1) The non-magnetic vibrator 2 is fabricated by forming the vibrator 2 made of non-magnetic material into a shape allowing a given resonant frequency to be obtained.

(2) The magnetic thin film 29 is formed on the fabricated non-magnetic vibrator 2. The magnetic thin film 29 is formed by depositing a ferromagnetic material made of iron (Fe), cobalt (Co), nickel (Ni), etc., or an alloy made of these materials, on the non-magnetic vibrator 2 of piezoelectric crystal, etc. by vacuum evaporation or sputtering process.

(3) The fabricated ferromagnetic vibrator 23 is magnetized using a permanent magnet 28 or electromagnet.

Figure 11:
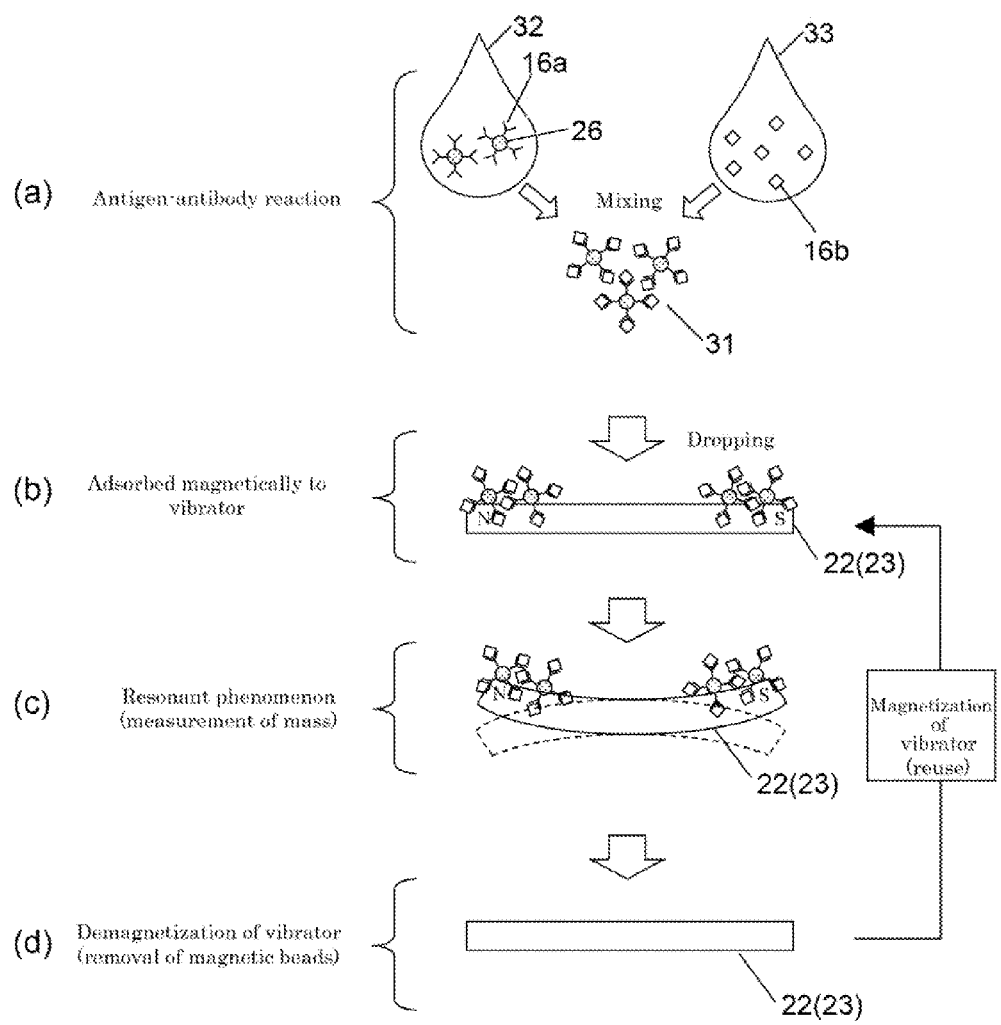
FIG. 11 is a chart describing a method of use of the resonant type mass sensor according to the third embodiment.

FIG. 11(*a*) to (*d*) is a chart describing a method of use of the resonant type mass sensor 20 according to the third embodiment of the present invention.

First, the magnetic measurement sample solution 31 described previously is prepared to examine the antigen-antibody complex reaction (See FIG. 11(*a*).). The magnetic measurement sample solution 31 is a mixture of a magnetic bead solution 32 and a sample solution 33. The magnetic bead solution 32 contains magnetic beads 26 to which the antibody 16a is adsorbed in advance. Meanwhile, the sample solution 33 contains antigen 16b, namely the target of antibody measurement. Appropriate amounts of the magnetic bead solution 32 and the sample solution 33 are mixed thoroughly to prepare a magnetic measurement sample solution 31.

Then, the magnetic measurement sample solution 31 is dropped on the vibrator 22, allowing it to be adsorbed onto the surface of the vibrator 22 and dried thoroughly, to make the magnetic measurement sample to be adsorbed onto the surface of the vibrator 22 (See FIG. 11 (b).).

The change in the resonant frequency of the measurement sample adsorbed onto the vibrator 22 (See FIG. 11(c).) is measured. Furthermore, the magnetic bead solution 32 only is dropped onto the vibrator 22, dried thoroughly, and the resonant frequency at that time is measured in advance. The magnetic measurement sample solution 31 is then dropped onto the vibrator 22, dried thoroughly, and by calculating the change in the resonant frequency at that time, the mass of the antigen 16b can be measured. The vibrator 23 as shown in FIG. 9 may be used instead of the vibrator 22 as shown in FIG. 8 as the vibrator. The same applies to the following description.

The magnetized measurement sample adsorbed onto the vibrator 22 can be removed from the vibrator 22 by demagnetizing the vibrator 22 (demagnetization), (See FIG. 11(d).).

In a biosensor using the antigen-antibody complex reaction, the antibody 16a is immobilized onto the sensing part (free end) of the vibrator 22 to collect specific molecules by the antigen-antibody complex reaction. Once the substance to be measured (antigen 16b) is immobilized onto the vibrator 22, the resonant frequency decreases in accordance with the mass (See FIG. 5.). Consequently, a slight change of the mass can be measured based on the change of the frequency (See FIG. 6.).

According to the third embodiment of the resonant type mass sensor 20, the magnetic measurement sample attaching to the vibrator 22 can be removed from the vibrator 22 by demagnetizing the magnetic property of the vibrator 22. For this reason, it is more easily to reuse the vibrator 22 (See FIG. 11(d).). According to this method, when the magnetic bead 26 modifying the antibody 16a is changed, a plurality of measurement substances can be measured with only one vibrator 22.

The present invention will hereafter be described further in detail by referring to examples.

EXAMPLES (Fabrication of the Vibrator)

Figure 12:
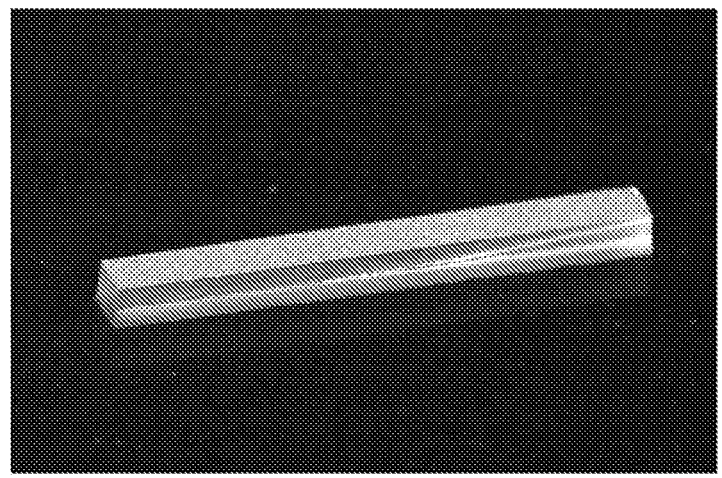
FIG. 12 is an optical image showing the appearance of the fabricated vibrator.

First, the vibrator 2 as shown in FIG. 1 was fabricated. An AT-cut crystal plate was selected as the material for the vibrator 2. The dimension of the vibrator 2 was determined to be 0.4 mm×0.4 mm×5 mm so that the resonant frequency of the vibrator of the primary-mode of the transverse vibration mode falls within a range approximately from 140 to 160 kHz. The AT-cut crystal plate is cut at the angle parallel to the surface 35° 15' inclined from the Z-axis of the crystal. FIG. 12 is an optical image showing the appearance of the fabricated vibrator 2.

Figure 13:
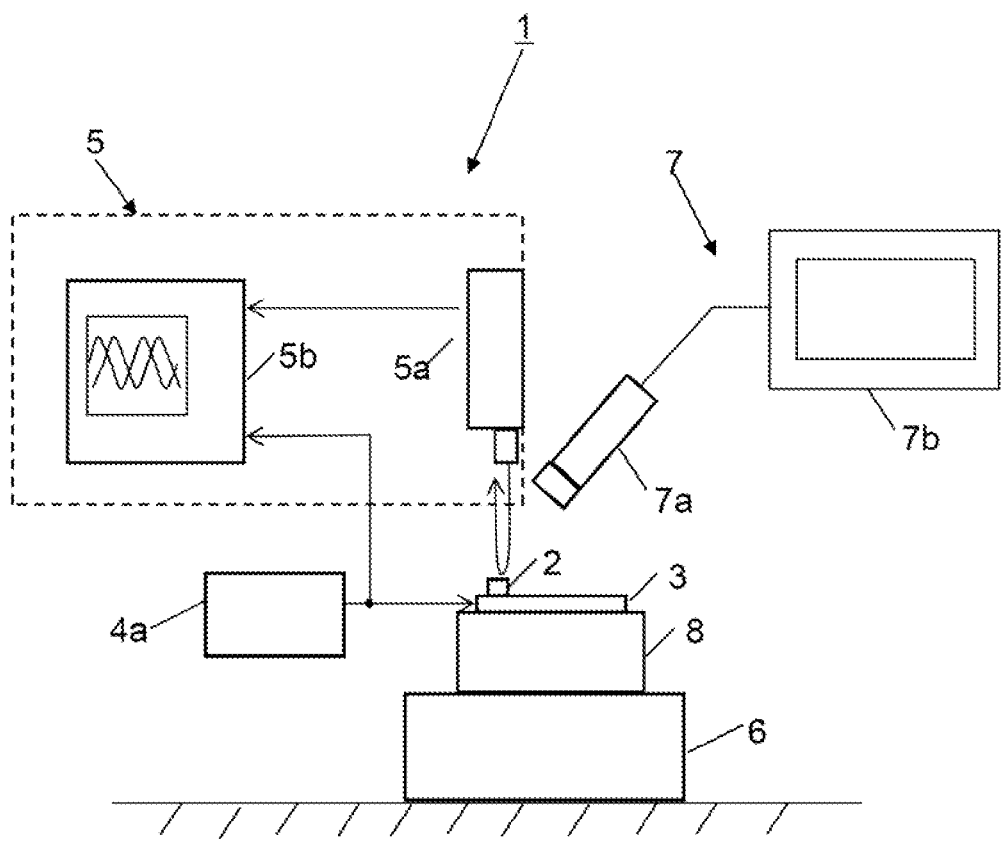
FIG. 13 is a block diagram showing the structure of the resonant type mass sensor fabricated in the example.

FIG. 13 is a block diagram showing the structure of the resonant type mass sensor 1 fabricated in the example. As shown in FIG. 13, the resonant type mass sensor 1 includes: the vibrator 2, the oscillator 3, the XYZ table 6 on which the vibrator 2 and the oscillator 3 are placed, a signal generator 4a for driving the oscillator 3, the detecting unit 5, and an observation unit 7. As the oscillator 3, a circular piezoelectric element (NEC Tokin Corporation, Japan, Material: N21) having a diameter of 20 mm and a thickness of 0.5 mm was used. The detecting unit 5 is made up of a microscope type laser Doppler vibrometer 5a (V100-S, Denshigiken Corporation, Japan), and an oscilloscope 5b. The observation unit 7 is made up of a charge-coupled device (CCD) camera 7a (VH-5000, KEYENCE CORPORATION, Japan) and a display 7b for monitoring.

A sponge 8 is inserted between the oscillator 3 made of the piezoelectric element and the XYZ table 6 (TSD-805S, Sigma Koki Co., Ltd., Japan) not to obstruct the vibration of the oscillator 3. The following description assumes that the oscillator 3 is made of the piezoelectric element.

The spot diameter of the microscope type laser Doppler vibrometer 5a is 40 μm. The positioning was performed by adjusting the position of the XYZ table 6 while observing the position using the CCD camera 7a so that the vibration velocity at the free ends of the vibrator 2 is measured by the microscope type laser Doppler vibrometer 5a.

The alternating voltage was applied to the piezoelectric element 3 by using the signal generator 4a (SG-4104, IWATSU TEST INSTRUMENTS) to vibrate the piezoelectric element 3. The microbeam-like vibrator 2 placed on the piezoelectric element 3 is resonates by receiving the vibration from the piezoelectric element 3. In other words, when the alternating voltage having a frequency close to the frequency of vibration of the microbeam-like vibrator 2 in the normal mode is applied to the piezoelectric element 3, the vibrator resonates at the frequency of vibration in the normal mode of itself. The vibration-velocity characteristics of this vibrator 2 were measured using the microscope type laser Doppler vibrometer 5a.

The output signal of the signal generator 4 and the vibration velocity measured by the microscope type laser Doppler vibrometer 5a were observed by using an oscilloscope (DS-5120B, IWATSU TEST INSTRUMENTS CORPORATION).

(Frequency Characteristics of the resonant Type Mass Sensor)

The relation between the resonant frequency and the mass of load was measured to evaluate the basic performance of the resonant type mass sensor 1. The frequency characteristics were measured by fastening a plate weight (KAGEYAMA Corp., Thickness; 0.1 mm) to the end of the vibrator 2 with adhesion as a load. Table 2 summarizes measurement conditions.

TABLE 2

| | |
|---|---|
| Applied voltage (V) | 7.07 |
| Resonant frequency of the vibrator (kHz) | 142.5 |
| Mass of the vibrator (mg) | 2 |
| Mass of the plate weight | 0.5, 1.0, 1.5, 2.0 |
| Speed conversion factor of the vibrator (m/sV) | 0.02 |

Figure 14:
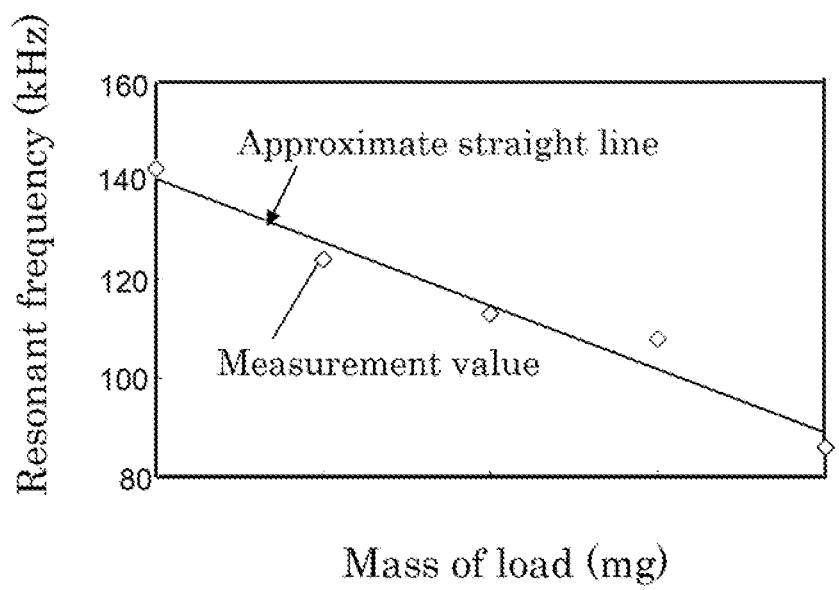
FIG. 14 is a chart showing the relation between the resonant frequency and the mass of load of the vibrator.

FIG. 14 is a chart showing the relation between the resonant frequency and the mass of load of the vibrator 2. The horizontal axis of the figure represents the mass of load (mg), and the vertical axis represents frequency. An approximate straight line to measurement values (marked with ◊) is shown by a solid line. Table 3 lists the measurements value of the resonant frequency taken under each mass of load.

As shown in FIG. 14 and Table 3, the resonant frequency was 142.5 kHz when the mass of load was 0, and the resonant frequencies were found to decrease with the increase of the mass of load.

TABLE 3

| Mass of load (mg) | Resonant frequency (kHz) |
|---|---|
| 0.0 | 142.5 |
| 0.5 | 124.0 |
| 1.0 | 113.0 |
| 1.5 | 108.0 |
| 2.0 | 86.0 |

(Measurement of Mass Using Protein)

BSA, a protein obtained by purifying bovine serum albumin, was attached to the vibrator 2, and the change of the resonant frequency at that time was measured.

The BSA was diluted with phosphate buffered saline (PBS) to prepare 0.5%, 3.0%, and 5.0% BSA solutions. For the analysis of total protein of the BSA solution, the calorimetric total protein assay kit (DC protein assay, Bio-Rad Laboratories, Inc., CA) and the microplate reader (ARVO MX, Perkin Elmer Inc.) were used.

Figure 15:
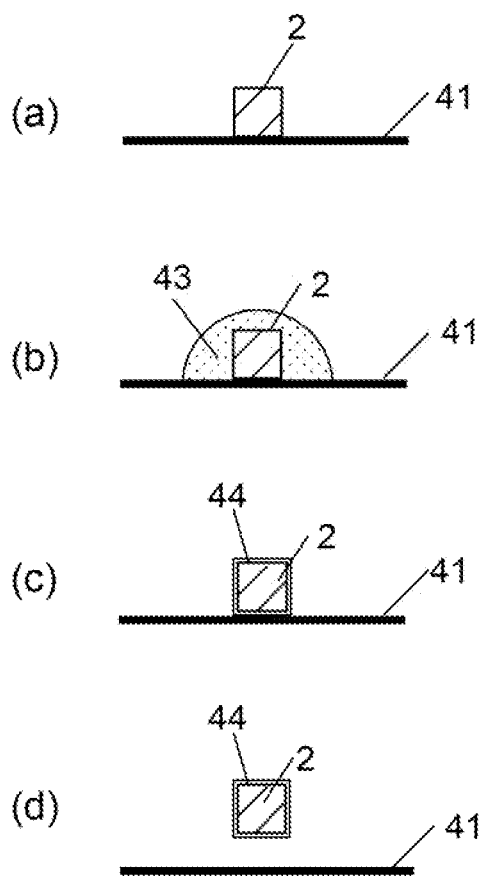
FIG. 15 is an illustration showing the BSA attachment process.

FIG. 15 is an illustration showing the BSA attachment process. As shown in FIG. 15, the vibrator 2 is disposed on a sample holder 41, and a 5 μl BSA solution 43 was then dropped onto the vibrator 2. The BSA 44 is attached to the vibrator 2 by leaving the BSA solution 43, that has been dropped onto the vibrator 2, for one hour to dry. The vibrator 2 to which the BSA 44 is attached can be obtained by removing the vibrator 2 from the sample holder 41.

Figure 16:
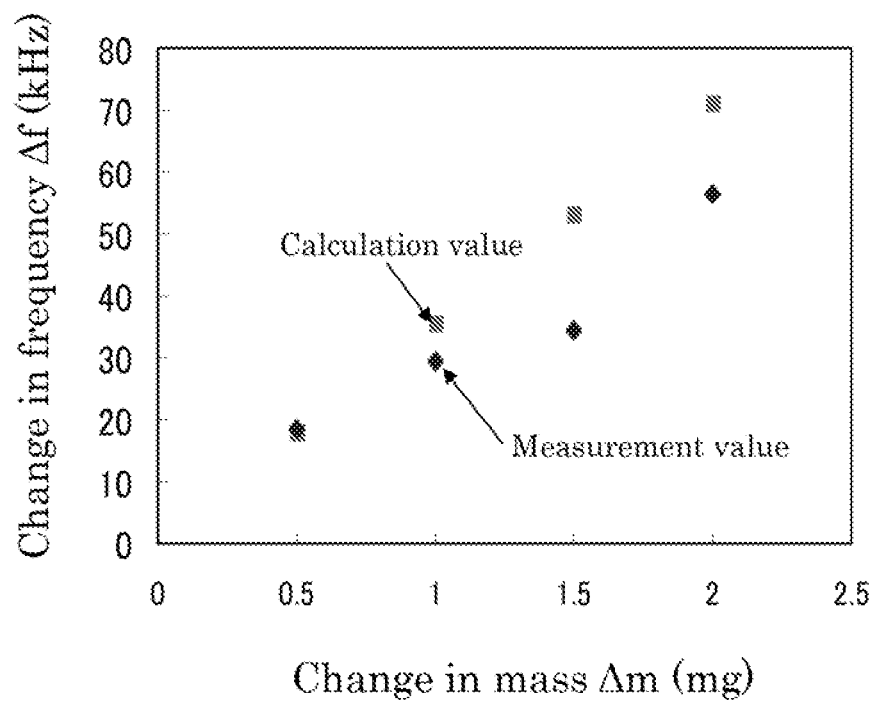
FIG. 16 is a chart showing the relation between the change of the mass and the change of the resonant frequency of the vibrator.

FIG. 16 is a chart showing the relation between the change of the mass and the change of the resonant frequency of the vibrator 2. In the figure, the horizontal axis represents the change of the mass Δ m (mg), and the vertical axis represents the change of the resonant frequency Δ f (kHz). Table 4 summarizes the relation between the change of the mass and the change of the resonant frequency.

As shown in Table 4, when the PBS solution was attached, the change of the mass was 0.03 mg and the change of the resonant frequency was 1.27 kHz.

When the 0.5% BSA solution 43 was attached, the change of the mass was 0.04 mg and the change of the resonant frequency was 1.59 kHz.

When the 3.0% BSA solution 43 was attached, the change of the mass was 0.07 mg and the change of the resonant frequency was 2.88 kHz.

When the 5.0% BSA solution 43 was attached, the change of the mass was 0.09 mg and the change of the resonant frequency was 3.42 kHz.

TABLE 4

| | PBS solution | 0.5% BSA solution | 3.0% BSA solution | 5.0% BSA solution |
|---|---|---|---|---|
| Change of mass Δ m (mg) | 0.03 | 0.04 | 0.07 | 0.09 |
| Change of resonant frequency Δ f (kHz) | 1.27 | 1.59 | 2.88 | 3.42 |

From the above measurement results, when the BSA solution 43 was attached, the measurement sensitivity to the mass was found to be 31.25 ng/Hz. Meanwhile, when weights of the same mass were respectively placed at both ends of the vibrator 2, the measurement sensitivity to the mass was measured to be 38.88 ng/Hz.

Figure 17:
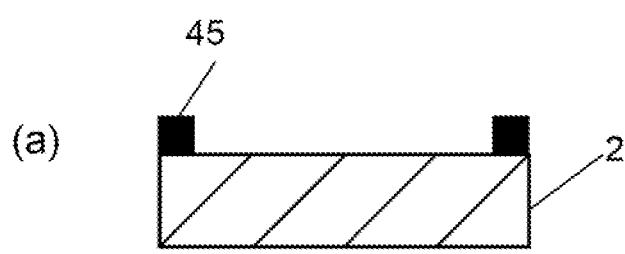
FIG. 17 shows cross-sectional views of the vibrator, wherein (a) exhibits the vibrator on which weights are disposed, and (b) exhibits the vibrator on which BSA is attached.
Figure 17:
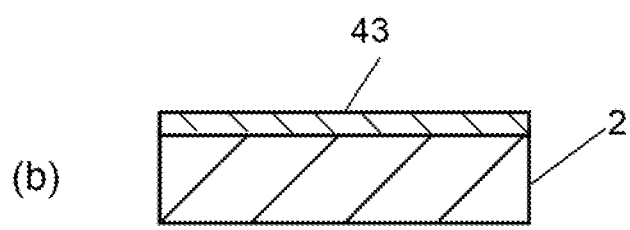

FIG. 17 shows cross-sectional views of the vibrator 2, where (a) exhibits the vibrator 2 on which weights 45 are placed, and (b) is the vibrator to which a BSA solution 43 is attached. The sensitivity to mass was smaller when the BSA solution 43 was attached than when the weights 45 were placed as shown in FIG. 17. For this reason, it is thought that the BSA solution 43 was attached to the entire surface of the vibrator 2, this attachment range expanding to the entire area of the vibrator 2, and thus the second moment of area of the vibrator 2 differed at the time of vibration.

(Measuring the Concentration of Total Protein Contained in Saliva)

The measurement of concentrations of total protein contained in human saliva will be described below. Saliva was collected as follows.

(1) Saliva was collected from four subjects.
(2) The collected saliva was subjected to centrifugal separation, and 300 μl of supernatant was taken out.
(3) The colorimetric total protein assay kit (DC protein assay; Bio-Rad Laboratories, Inc., CA) and the microplate reader (ARVO MX, Perkin Elmer Inc.) were used for the analysis of total protein. Saliva of the highest concentration was selected and used for the following experiment.

Figure 18:
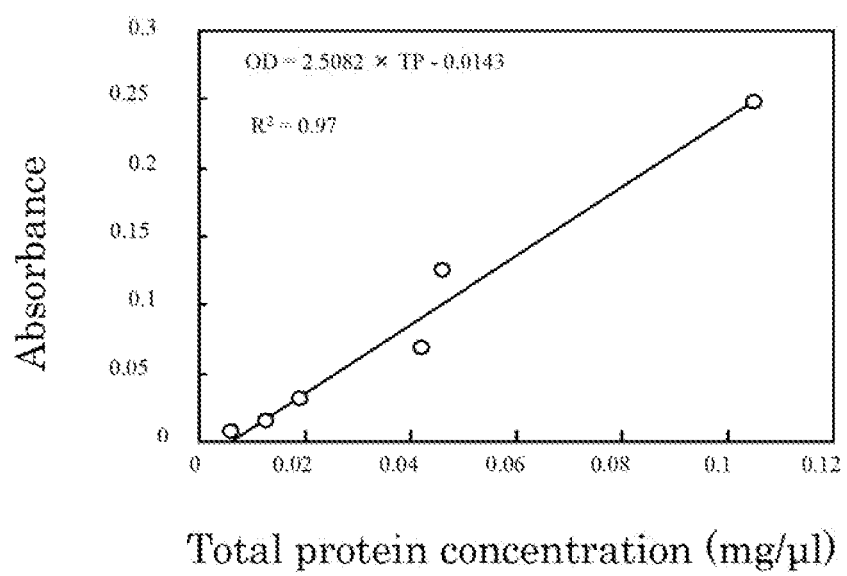
FIG. 18 is a chart of a calibration curve showing the relation between total protein concentrations, which was measured separately, and the absorbance of a microplate reader.

FIG. 18 shows a calibration curve showing the relation between the total protein concentration, which has been measured separately, and the absorbance of the microplate reader. The absorbance was converted into the total protein concentration using the correlation as shown in FIG. 18.

(4) The selected saliva (sample solution) was concentrated using a centrifugal evaporator (at 37° C. for 15 to 30 minutes) to produce sample solutions twice and four-times concentrated.
(5) The 5 μl of sample solution was dropped to the vibrator 2 made of crystal, and dried at 25° C. for one hour.
(6) Using the resonant type mass sensor 1 as shown in FIG. 13, the resonant spectrum of the vibrator 2 to which the saliva was attached was measured by a spectrum analyzer under the following conditions.
  Applied voltage: 7.07 [V]
  Measurement range: 5 [kHz] before and after the resonant frequency
(7) The sample attaching to the crystal vibrator 2 was washed using a detergent.
(8) The vibrator 2 made of crystal was dried.
(9) Procedures from (1) to (8) were followed for each of the samples.

Figure 19:
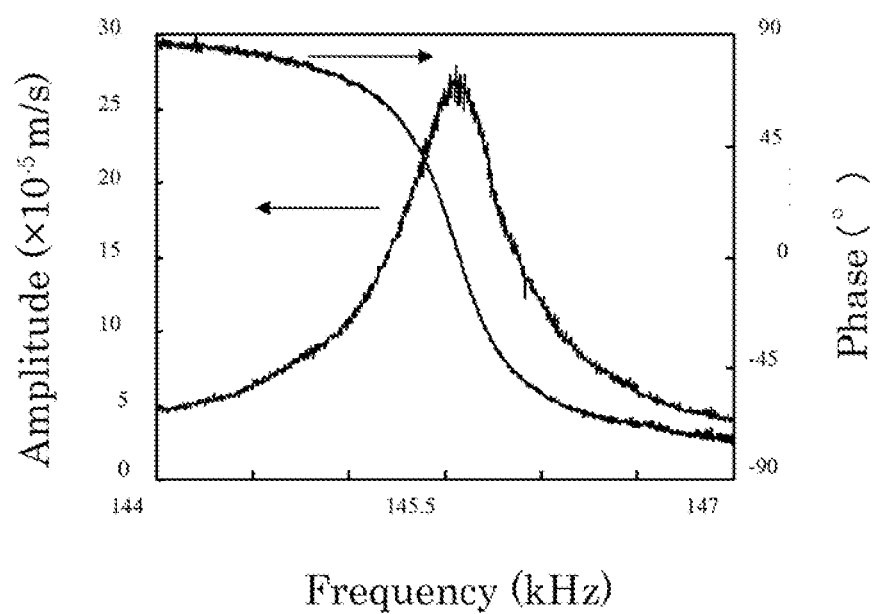
FIG. 19 is a chart showing the measurement result of resonance spectrum of the vibrator using a spectrum analyzer when the saliva of total protein concentration of 0.2 (mg/μl) was used.

FIG. 19 is a chart showing the result of measurement of the resonant spectrum of the vibrator 2 carried out using the spectrum analyzer when the saliva of total protein concentration of 0.2 (mg/μl) was used. The horizontal axis in the figure represents frequency (kHz), the left vertical axis represents amplitude ($\times 10^{-5}$ m/s), and the right vertical axis represents phase (°). It is apparent that the resonant frequency of the vibrator 2 changed by 2.7 kHz from 143 kHz, the value obtained when there was no attachment, to 145.7 kHz.

Figure 20:
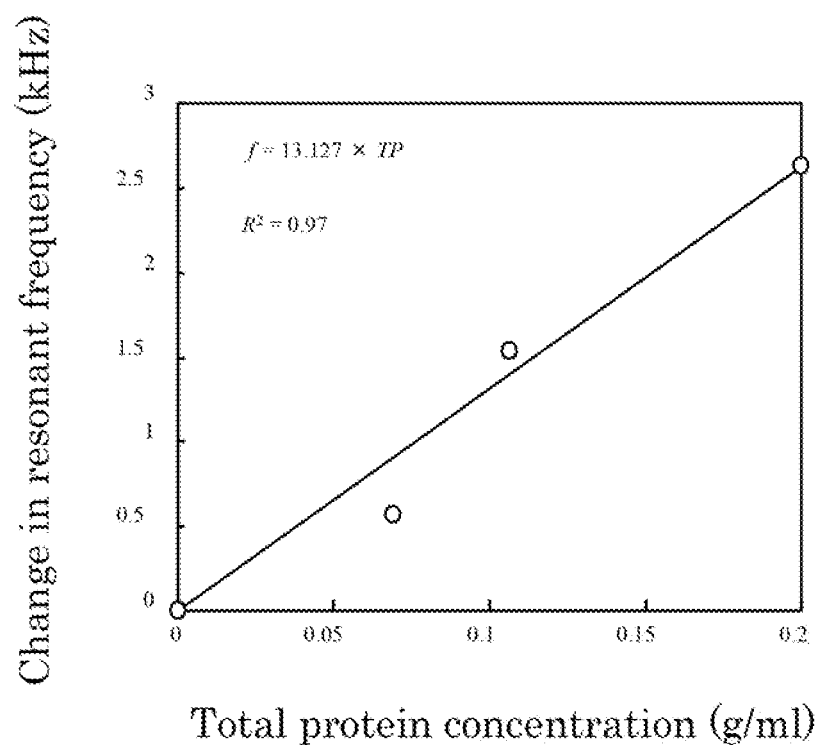
FIG. 20 is a chart showing the relation between the total protein concentration of a sample solution and the resonant frequency of the vibrator.

FIG. 20 is a chart showing the relation between the total protein concentrations of the sample solution and the resonant frequency of the vibrator 2. The vertical axis of the figure represents the change in the resonant frequency (kHz), and the horizontal axis represents the total protein concentration (g/ml). As shown in FIG. 20, the change of the resonant frequency f (kHz) is represented by the formula (4) as shown below:

$$f = 13.127 \times TP \quad (4)$$

In the above formula, TP represents total protein concentrations (g/ml).

As shown in FIG. 20, since the change of the resonant frequency is 1.3172 kHz when the total protein concentration is 0.1 g/ml, the measurement sensitivity to total protein concentrations is found to be 76.2 (μg/ml)/Hz. Since the frequency resolution of the microscope type laser Doppler vibrometer 5a used to measure the change of the resonant frequency was 1 mHz ($10^{-3}$ Hz), the measurable total protein concentration is estimated to be 76.2 ng/ml.

From the results described above, the resonant type mass sensor 1 of the present invention was found to have measurement sensitivity sufficient to measure the concentration of a trace amount of protein contained in saliva.

The present invention is not limited to the examples described above, but various variations are allowed within the scope of the claims of the present invention. Needless to say, they are all included in the scope of the present invention.

What is claimed is:

1. A resonant type mass sensor, comprising:
an oscillator;
a vibrator placed on the oscillator; and
a detecting unit for detecting the resonant frequency of the vibrator, characterized in that the vibrator and the oscillator are not coupled mechanically, and the vibrator is not mechanically coupled to any members.

2. The resonant type mass sensor as set forth in claim 1, characterized in that the vibrator is placed on the oscillator in unrestricted state.

3. The resonant type mass sensor as set forth in claim 1 or 2, characterized in that the vibrator is excited by the oscillator at frequencies close to the resonant frequency of the vibrator.

4. The resonant type mass sensor as set forth in claim 1 or 2, characterized in that the oscillator is made of a piezoelectric element.

5. The resonant type mass sensor as set forth in claim 4, characterized in that the piezoelectric element vibrates in response to the application of alternating voltage.

6. The resonant type mass sensor as set forth in claim 1 or 2, characterized in that the vibration of the vibrator is represented by a standing wave.

7. The resonant type mass sensor as set forth in claim 1 or 2, characterized in that the vibrator has a shape of an elongated pillar.

8. The resonant type mass sensor as set forth in claim 7, characterized in that the vibration mode of the vibrator is a transverse vibration mode.

9. The resonant type mass sensor as set forth in claim 1 or 2, characterized in that the vibrator is made of a piezoelectric crystal.

10. The resonant type mass sensor as set forth in claim 9, characterized in that the piezoelectric crystal is a crystal or PZT.

11. The resonant type mass sensor as set forth in claim 10, characterized in that the crystal is obtained by AT cutting.

12. The resonant type mass sensor as set forth in claim 1 or 2, characterized in that the vibrator has a molecular recognition means to recognize the molecules of a substance to be measured.

13. The resonant type mass sensor as set forth in claim 12, characterized in that the molecular recognition means collects specific molecules by antigen-antibody reaction.

14. The resonant type mass sensor as set forth in claim 1 or 2, characterized in that the vibrator contains at least a magnetizable part.

15. The resonant type mass sensor as set forth in claim 14, characterized in that magnetic beads to which antibody and/or antigen are/is immobilized are adsorbed magnetically to the magnetizable part.

16. The resonant type mass sensor as set forth in claim 14, characterized in that the magnetizable part is made of a ferromagnetic material.

17. The resonant type mass sensor as set forth in claim 16, characterized in that the ferromagnetic material is made of any one of soft iron, silicon steel, ferrite, cobalt, nickel, and alnico magnets.

18. The resonant type mass sensor as set forth in claim 1, characterized in that the detecting unit comprises a light-emitting device and a photo-sensitive device, and the unit includes a means to detect any one of frequency, displacement, velocity, and acceleration.

19. The resonant type mass sensor as set forth in claim 18, characterized in that the detecting unit includes a microscope type laser Doppler vibrometer.

* * * * *